United States Patent [19]
Takeda et al.

[11] Patent Number: 5,315,847
[45] Date of Patent: May 31, 1994

[54] WASHING MACHINE

[75] Inventors: Yoshiaki Takeda, Hitachi; Katuyosi Miwano, Ibaraki; Noboru Fujita, Hitachi, all of Japan

[73] Assignee: Hitachi, Ltd., Tokyo, Japan

[21] Appl. No.: 859,885

[22] Filed: Mar. 30, 1992

[30] Foreign Application Priority Data

Mar. 29, 1991 [JP] Japan ................. 3-066013
Mar. 29, 1991 [JP] Japan ................. 3-066014

[51] Int. Cl.$^5$ .............................. D06F 33/02
[52] U.S. Cl. ........................ 68/12.02; 68/12.27; 324/439
[58] Field of Search ............. 68/12.02, 12.27; 324/439

[56] References Cited

U.S. PATENT DOCUMENTS

| | | | |
|---|---|---|---|
| 3,645,669 | 2/1972 | Rausch | 68/12.27 X |
| 4,091,833 | 5/1978 | Ellis et al. | 137/93 |
| 4,237,565 | 12/1980 | Torita et al. | 68/12.27 X |
| 4,257,708 | 3/1981 | Fukuda | 356/435 |

FOREIGN PATENT DOCUMENTS 2412638 12/1978 France .
22689 1/1987 Japan ................. 68/12.02
29557 6/1988 Japan ................. 68/12.02

Primary Examiner—Philip R. Coe
Attorney, Agent, or Firm—Antonelli, Terry, Stout & Kraus

[57] ABSTRACT

A washing machine comprises a washing/dehydrating tank, a water storage tank in which the washing/dehydrating tank is disposed, and a sensor for detecting an electric conductivity of washing water in the washing-/dehydrating tank and the water storage tank. The sensor is provided with a pair of electrodes to take into account a variation of an electric resistance of the washing water therebetween, which is representative of the electric conductivity of the washing water, thereby controlling a washing operation of the washing machine. The sensor has a CR oscillation circuit including a resistance which represents the electric conductivity of the water between the electrodes. A variation of the electric conductivity of the washing water is converted into an oscillation frequency variation of the oscillation circuit, and the operation of the washing machine is controlled on the basis of the thus varying oscillation frequency.

14 Claims, 5 Drawing Sheets

WASHING MACHINE

BACKGROUND OF THE INVENTION

The present invention relates to a washing machine which detects a detergent content and a soiled condition of washing water to control a washing operation, and also to a conductivity detecting sensor for detecting an electric conductivity of the washing water.

In a conventional washing machine, a detergent content and a soiled condition of washing water are surmised by detecting transmittance of light through the washing water to control an washing operation of the washing machine.

Detecting means of the light transmittance includes a transparent pipe provided in a drain passage of the washing machine, a luminous element and a light receiving element which are provided opposite to each other, with the transparent pipe being interposed therebetween. In this type of detecting means, the detection accuracy is adversely affected when the pipe gets contaminated. That is, even if there is no water in the washing machine or the water in the washing machine is clean, the detecting means erroneously detects that the water is soiled due to contaminants on the pipe.

SUMMARY OF THE INVENTION

The present invention aims at solving the above-described problem and has an object of providing a washing machine in which an electric conductivity of washing water is directly determined to control an washing operation of the washing machine.

Another object of the invention is to improve the detection accuracy of a conductivity detecting sensor for detecting an electric conductivity of washing water by taking into account positioning of the sensor and a shape thereof into consideration.

Still another object of the invention is to improve the performance, lifetime, durability and safety of a conductivity detecting sensor.

A washing machine according to the present invention comprises a washing/dehydrating tank, a water storage tank in which the washing/dehydrating tank is disposed and a conductivity detecting sensor for detecting an electric conductivity of washing water in the washing/dehydrating tank and the water storage tank, wherein the sensor is provided with a pair of electrodes adapted to take into account a variation of electric resistance of the washing water between the electrodes which represents the conductivity, thereby controlling an washing operation of the washing machine.

More specifically, according to the invention, a CR oscillation circuit is connected with the electrodes of the conductivity detecting sensor through an insulation transformer. An oscillation frequency caused by the resistance variation between the electrodes, is counted to detect the conductivity of the washing water.

BRIEF DESCRIPTION OF DRAWINGS

The accompanying drawings illustrates an embodiment of the invention, wherein.

DETAILED DESCRIPTION OF EMBODIMENT

Figure 1:
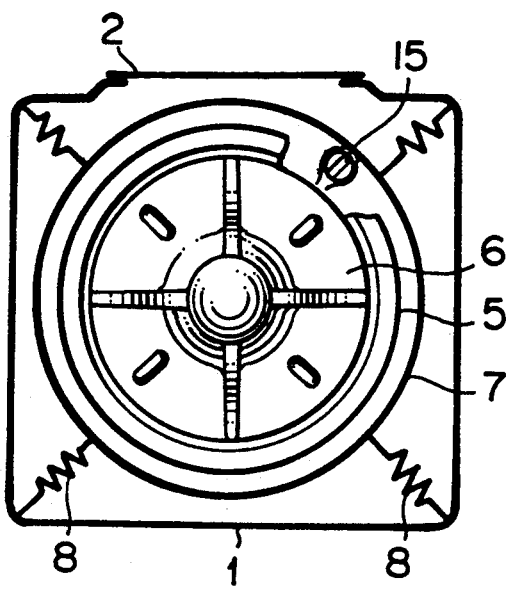
FIG. 1 is a top plan view of a washing machine from which a top cover has been removed.
Figure 2:
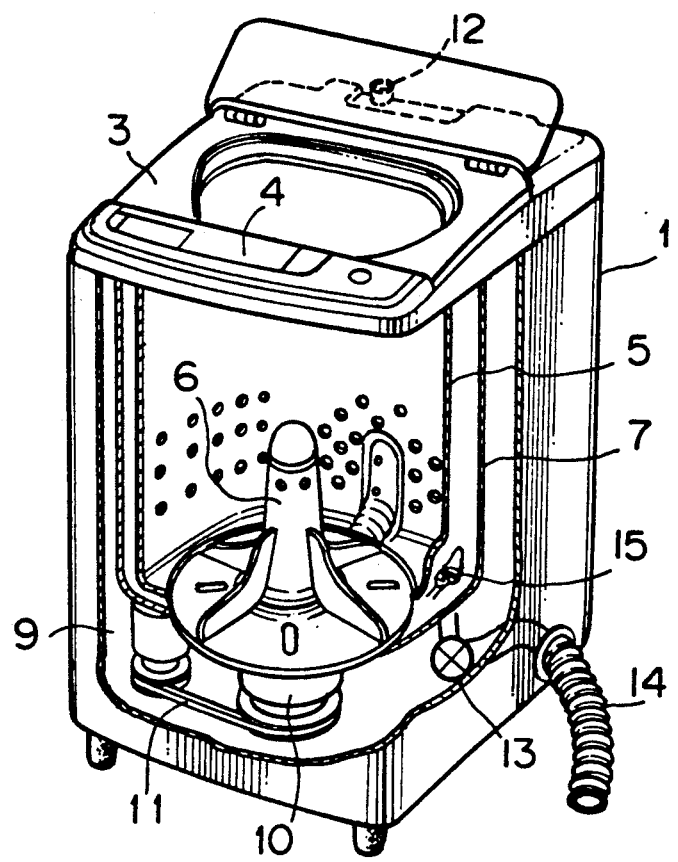
FIG. 2 is a perspective, partial cross-sectional view of the washing machine.
Figure 3:
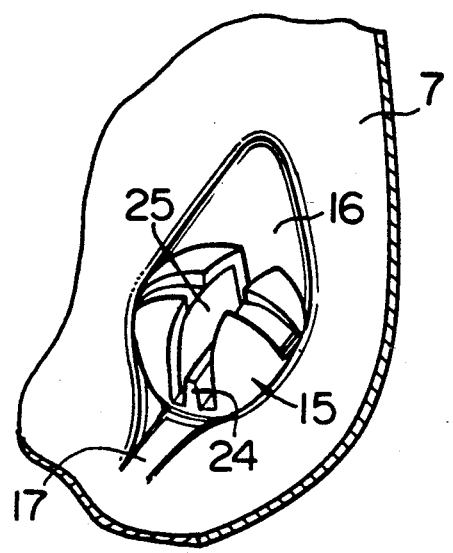
FIG. 3 is a perspective view showing an attachment portion of an electric conductivity detecting sensor constructed in accordance with the present invention.

As shown in FIGS. 1, 2 and 3, a washing machine includes an outer frame 1 and a rear cover 2 which is detachably attached to the rear side of the outer frame 1 with screw fasteners on the line. The outer frame 1 is made of a steel plate, and a top cover 3 (FIG. 2) is attached onto the upper portion of the outer frame. The top cover 3 is provided at its front side with an operation panel 4 (FIG. 2) for controlling operations of the washing machine.

A washing/dehydrating tank 5 has an agitation blade 6 provided on an inner bottom portion thereof. The agitation blade 6 is rotatably mounted on the washing-/dehydrating tank 5. A water storage tank 7, in which the washing/dehydrating tank 5 is disposed is suspended by the outer frame 1 through vibration isolating springs 8. A motor 9 is fixed on the lower side of the water storage tank 7. A speed reduction mechanism and a clutch casing 10, having a clutch therein, are also attached on the lower side of the water storage rank 7. Rotation of the motor 9 is transmitted through a belt 11 to a rotational member within the clutch casing 10. The rotational member in the clutch casing 10 is connected to the rotary blade 6 and the washing/dehydrating tank 5. According to a connecting or disconnecting operation of the clutch, the rotation of the motor 9 is transmitted to only the agitation blade 6 or both of the agitating blade 6 and the washing/dehydrating tank 5. This type of washing machine having the washing/dehydrating tank 5 is a so-called fully automatic washing machine.

A coupling connector 12 for a water pipe is provided on the upper rear side of the top cover 3 to supply water to the washing/dehydrating tank. A drain valve 13 for discharging the water of the water storage tank 7 is provided on the lower side of the water storage tank 7. When the drain valve 13 is opened, the water flows out of the tank through a drain hose 14.

The water storage tank 7 has an electric conductivity detecting sensor 15 fixed to one corner portion on the bottom thereof. The bottom corner portions of the water storage tank 7 are formed in an arcuate shape which extends upwardly apart from the bottom of the outer frame 1.

The sensor 15 is mounted in a recessed portion 16 which is formed by providing a recess in the bottom of the water storage tank 7. The recessed portion 16 is in a shape which extends outwardly, and the sensor 15 is maintained in the recessed portion 16 so that head portion thereof does not extend beyond the inner surface of the water storage tank 7. Although the head portion of the sensor 15 may extend beyond the inner surface of the water storage to some extent, if the extension is too large, the head portion would undesirably come in contact with the outer surface of the washing/dehydrating tank 5.

The sensor 15 is attached to the water storage tank 7 from the outside thereof. The recessed portion is located in the rear of the water storage tank 7 so as to be on the side of the rear cover 2. Maintenance of the sensor 15 can be readily accomplished from the outside of the water storage tank 7 by removing the rear cover 2.

The shape of the recessed portion 16 is substantially ellipsoidal when viewed from an interior of the water storage tank 7. The recessed portion 16 is arranged such that a longitudinal axis of its ellipse-like shape is substantially perpendicular to a rotating direction of the washing/dehydrating tank 5. The recessed portion 16 is formed with a water passing groove 17 at the inner end of its longitudinal axis.

As shown in FIGS. 3, 4, 5 and 6, the sensor 15 includes a sensor casing 18 fashioned of a synthetic material such as ABS resin. The use of ABS resin will improve, as well as a chemical proof of the casing.

The sensor casing 18 includes an electrode holder 19 and an electric part container 20 which are open on the rear sides thereof. The open portions of the electrode holder 19 and the container 20 are formed together with a circuit board housing 21. The electric part container 20 is provided adjacent to the electrode holder 19. The electric part container 20 has sections for receiving a transformer and capacitors.

Figure 6:
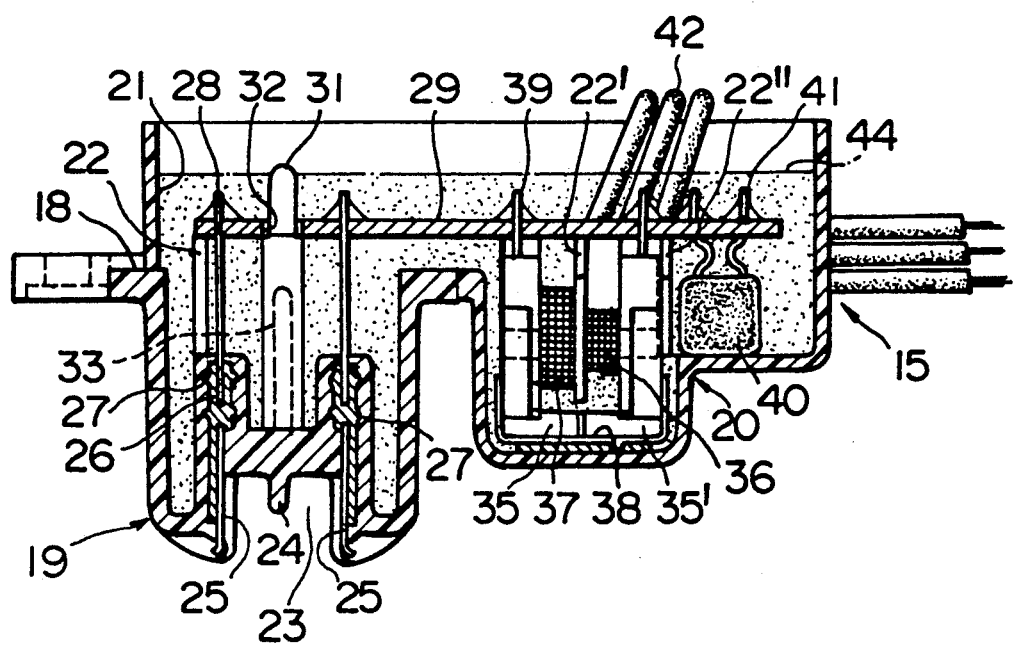
FIG. 6 is a cross-sectional view taken along the line VI—VI' in FIG. 4.

The sensor casing 18 is formed with supporting ribs 22, 22', 22" for a circuit board on the inner wall surface thereof. The electrode holder 19 has a cylindrical contour, and a groove 23 shown in FIG. 6, is formed in a distal end. A head portion of the electrode holder 19, which is the distal end thereof, is substantially spherical. The groove 23 is provided with an upright separator 24 (FIG. 6) at the center of the bottom thereof. The upright separator 24 is so formed as to extend in the longitudinal direction of the groove 23.

A pair of electrodes 25 fashioned of stainless steel are provided on the electrode holder 19. A detector of each electrode 25 has a plate-like plane surface. The electrodes 25 are disposed on the respective, opposite inner walls of the groove 23 with their plane surfaces being opposite to each other and exposure. The thus exposed, opposite surfaces come in contact with washing water for detection of an electric resistance which is representative of an electric conductivity of the washing water. Each electrodes 25 may be directly embedded in the ABS resin of the electrode holder 19. In the illustrated embodiment, however, each electrode has a double-layer mold structure. More specifically, the electrode 25 is coated with a layer 26 of silicone rubber before being molded with the ABS resin. The coating layer 26 is formed such that a bonding resin is first applied on the electrode 25, the silicone rubber is further applied on the bonding resin layer and, then, the outermost silicone rubber is vulcanized. The bonding portion between the electrode 25 and the coating layer 26 is superior in water-tightness and air-tightness. At the time when molding with the ABS resin, since the resin is injected into a mold under a high pressure, the coating layer 26 of the silicone rubber is held at the electrode holder 19 in a compressed state by the molding. The bonding portion between the coating layer 26 and the ABS resin is also superior in both of water-tightness and air-tightness thanks to the above-described compressed condition of the coating layer 26. The water-tightness of the bonding portion is maintained even if the electrode holder 19 expands or contracts due to a variation of temperature, so that water never enters the sensor casing from the holding portion for the electrode 25.

The coating layer 26 of each electrode 25 extends for a longer length on the rear surface thereof. This is because of improving the water-tightness and air-tightness.

Two circular projections 27 are formed on the outer periphery of each coating layer 26. This formation of projections further improves the water-tightness and air-tightness and produces an effect of preventing the electrode from slipping out of the holding portion.

The other end of each electrode 25, serving as a connection terminal, extends to the open portion on the rear side of the electrode holder 19. Each electrode 25 has two connection legs 28 on its connection terminal side. These two connection legs 28 are inserted in corresponding apertures of the circuit board 29 and fixed by soldering. Each electrode 25 has a substantially C-shaped opening formed on its connection terminal side, which opening is situated in the vicinity of the connection legs 28. The connection legs 28 can readily bend in the longitudinal direction of the electrode 25 due to the provision of the opening 30 and, therefore, no excessive force acts on the soldered and fixed portions of the connection legs 28.

A support pillar 31 is formed in the electrode holder 19 to extend at the center of the open portion on the rear side thereof. The support pillar 31 is inserted in a positioning hole 32 of the circuit board 29 to thereby fix the attachment position of the circuit board 29. The support pillar 31 includes a stepped portion on which the circuit board 29 is supported. The support pillar 31 is formed on its outer periphery with reinforcement ribs 33 which extend in the axial direction of the pillar.

An insulation transformer 34 has a structure in which a primary coil 36 and a secondary coil 37 are wound around a pair of cores 35, 35' and these cores 35, 35' are clamped by a fixture 38. The insulation transformer 34 is accommodated in the transformer receiving section of the sensor casing 18, with a cushion of a foamed material being disposed below the bottom of the insulation transformer 34. Terminals 39 of the insulation transformer 34 are inserted into reception holes of the circuit board 29 and so as to be fixed thereto.

A capacitor 40 is a filter capacitor for use in an oscillation circuit. The capacitor 40 is housed in the capacitor receiving section of the sensor casing 18. Terminals 41 of the capacitor 40 are also inserted in reception holes of the circuit board 29 and soldered to be fixed thereto.

It is better in view of the work efficiency to perform the soldering fixation of the connection legs 28 of the electrodes 25, the terminals 39 of the insulation transformer 34 and the terminals 41 of the capacitor 40 at one time. More specifically, the insulation transformer 34 and the capacitor 40 are first inserted and set in the sensor casing 18 and, then, the circuit board 29 is inserted in the sensor casing 18 to be set on the supporting ribs 22, 22', 22". At this time, since the support pillar 31 is inserted in the positioning hole 32 to locate the circuit board 29 in place, the terminals 39, 41 and connection legs 28 of the above components are also inserted in the corresponding reception holes at once. Accordingly, if fixing the terminals 39, 41 and the connection legs 28 by soldering after the above setting, the soldering is completed all at once with a good manufacturing efficiency.

Lead wires 42 are three codes for a power source and for outputting detection signals. These lead wires 42 may be fixedly soldered simultaneously with the above soldering fixation. However, since these lead wires 42 unfavorably sway to and fro, it is preferable that the lead wires 42 have previously been soldered to the circuit board.

Figure 4:
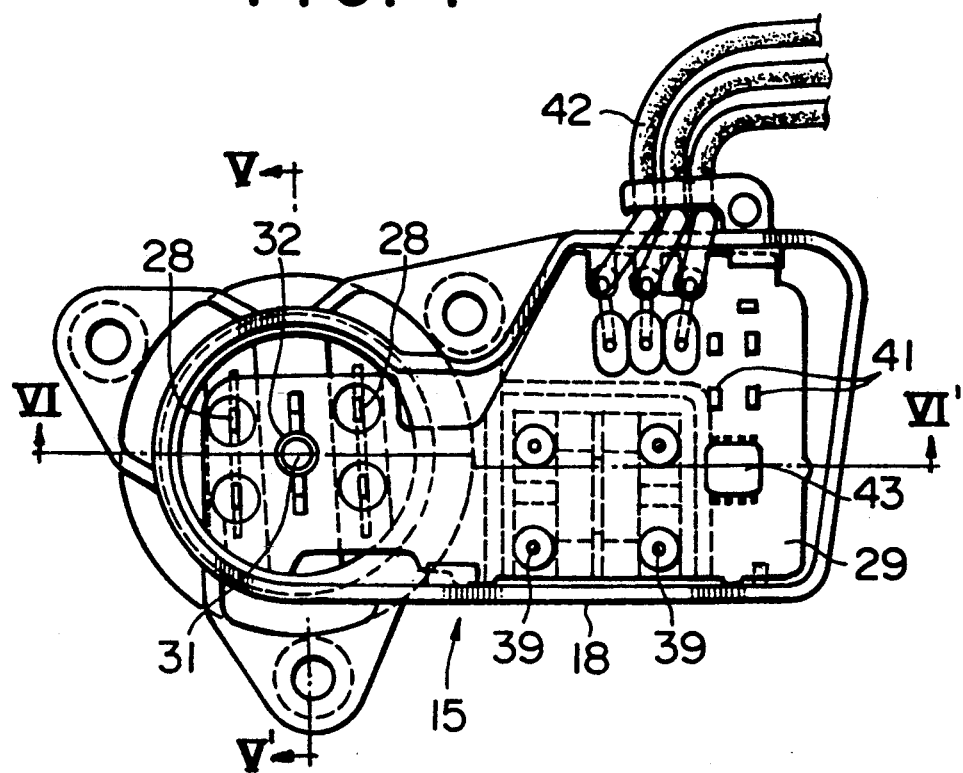
FIG. 4 is rear plan view of a sensor casing of the water conductivity detecting sensor of the present invention.
Figure 7:
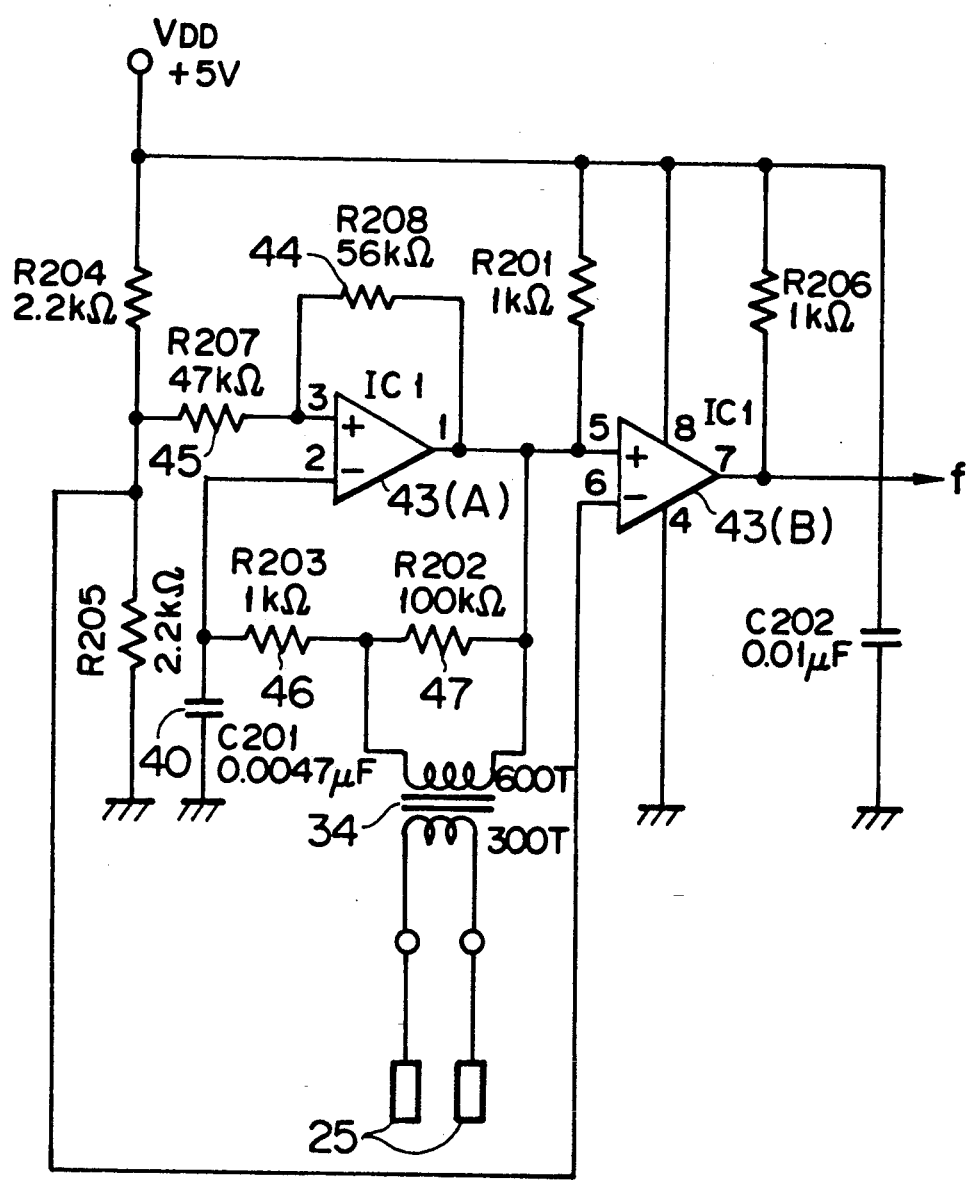
FIG. 7 is a wiring diagram of an oscillation circuit of the sensor.

On the circuit board 29, electric and electronic component parts of an oscillation circuit as illustrated in FIG. 7 are installed. FIG. 4 shows the state of these component parts' being actually mounted on the circuit board. Although resistors and capacitors are mounted in addition to inverters 43, the resistors and the capacitors are omitted in the drawing because they are too small in size. The inverters 43, the resistors and the capacitors have previously been connected to the circuit board prior to the above-described soldering fixation.

After completion of setting of the circuit board 29 and the various type of soldering workings, urethane resin for moisture proofing is poured into the sensor casing 18.

Figure 5:
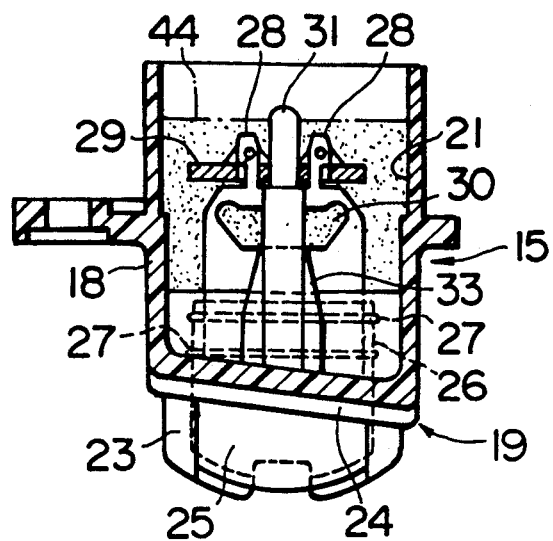
FIG. 5 is a cross-sectional view taken along the line V—V' in FIG. 4.

The sensor casing 18 is filled with the urethane resin until the resin reaches a level as indicated by a line 44 in FIGS. 5 and 6. The urethane resin is so poured so as to completely cover the insulation transformer 34, the capacitor 40 and the terminals of the electrodes 25 to tightly seal them. At the same time, the resin completely seals the overall of the component parts in the sensor casing 18 including the upper and lower surfaces of the circuit board 29 and the soldered and fixed portions of the terminals. The sealing structure of the sensor 15 therefore remarkably superior in moisture proofing. Moreover, the urethane resin also serves to securely fix the circuit board 29 and the various types of electric and electronic component parts mounted on the circuit board 29 in the sensor casing 18. The urethane resin possesses a good adhesive property with respect to the ABS resin of the sensor casing 18 so that the parts accommodated in the sensor casing 18 can be securely held.

The urethane resin is superior in moisture proofing, but it thermally expands or contracts to a large extent. Because the electrodes 25 are embedded in and secured to the sensor casing 18 by molding, an excessively large force may act on the soldered and fixed portions of the connection legs 28 when the urethane resin expands. In order to reduce this force, the substantially C-shaped opening 30 in provided in the vicinity of the connection legs 28 of each electrode 25. The opening 30 enables proximal portions of the connection legs 28 to be easily deformed in the axial direction of the electrode 25. The connection legs 28 are bent in accordance with the thermal expansion of the urethane resin. The excessively large force is not therefore exerted on the soldered and fixed portions so that the connection legs 28 are not disconnected from the circuit board 29.

The cushion of the foamed material is disposed below the bottom of the insulation transformer 34 for the purpose of reducing an unfavorable force which, otherwise, would be caused by the thermal expansion of the urethane resin and act on the insulation transformer 34. Since the insulation transformer 34 comprises the two cores 35, 35' clamped by the metal fixture 38, a gap between opposing surfaces of the cores 35, 35: will vary unless the unfavorable force is reduced by the foamed material. If the gas changes, the characteristic or performance of the insulation transformer 34 varies, which, in turn adversely affect a detection accuracy of the electric conductivity detecting sensor 15. In order to avoid this phenomenon, the foamed material is interposed as a cushion between the bottom of the insulation transformer 34 and the sensor casing 18.

The oscillation circuit shown in FIG. 7 is an astable multivibrator circuit which consists essentially of an inverter 43(A), resistors 44, 45 for feeding back from the output side to the input side of the inverter 43(A), the capacitor 40, and resistors 46, 47.

Assuming here that a voltage Ec at the capacitor 40 on the minus input terminal side of the inverter 43(A) is less than a voltage E+ at a plus input terminal of the inverter 43(A), a voltage Eo at an output terminal of the inverter 43(A) is at a high level. Thus, the capacitor 40 is charged through the resistors 44, 45. When the charging of the capacitor 40 progresses and the voltage Ec at the capacitor 40 becomes higher than the voltage E+ at the plus input terminal of the inverter 43(A), the voltage Eo at the output terminal of the inverter 43(A) turns over to be at a low level. At this time, therefore, the inverter 43(A) is charged through the resistors 44, 45 from the capacitor 40. In the course of time, when the voltage Ec at the capacitor 40 again becomes lower than the voltage E+ at the plus input terminal of the inverter 43(A), the voltage Eo at the output terminal of the inverter 43(A) is reversed to the high level. Oscillation continuously occurs by repetition of the above-described operations.

In this embodiment, the oscillation circuit is provided with a further inverter 43(B) at a back stage of the inverter 43(A). This inverter 43(B) rectifies the rectangular wave form of the oscillation output.

An oscillation frequency of an oscillation circuit is generally expressed by the following formula:

$$F = \frac{1}{2RC}$$

In this embodiment, since the electrodes 25 of the sensor 15 are connected to the resistor 47 through the insulation transformer 34, the oscillation frequency is expressed by the following formula:

$$F = \frac{1}{2C\left(R_1 + \frac{R_2 R_x}{R_2 + R_x}\right)}$$

where
C . . . capacitor 40
$R_1$ . . . resistor 46
$R_2$ . . . resistor 47
Rx . . . an electric-conductivity resistance between the electrodes.

As apparent from the above formula, the oscillation frequency varies in accordance with a change of the conductivity resistance between the electrodes 25. Therefore, it is possible to know a soiled condition of the washing water from the oscillation frequency.

The oscillation circuit is incorporated in the sensor 15 to increase the detection accuracy. On the other hand, in the case that the oscillation circuit is located in the control panel at the upper portion of the washing machine and connected through long lead wires to the electrodes 25 which are attached on the bottom of the water storage tank 2 of the washing machine, noises and a variation in impedance between the lead wires change the oscillation frequency and it would be impossible to correctly detect the soiled condition of the washing water. In the embodiment, to avoid the drawback due to the noises and the impedance variation, the oscillation circuit is mounted in the sensor casing 15 together with the sensor 15.

The insulation transformer 34 ensures a safety of the washing machine. The electrodes 25 are immersed in the washing water, but they are insulated from the power source side by the insulation transformer 34 and the operation of the washing machine can be carried out in safety.

Although a voltage supplied to the oscillation circuit is 5 V, there is a possibility that the circuit will have the voltage of the power source through an earthing circuit. In the embodiment, however, the voltage of the power source is mover applied to the electrodes 25 because they are connected to the oscillation circuit through the insulation transformer 34.

Since the number of turns of the coil on the primary side of the insulation transformer 34 is half of that on the secondary side thereof, a voltage to be applied to the electrodes 25 is low, i.e., 2.5 V and, therefore, is safe for an operator.

A detection signal of the soiled condition of the washing water from the inverter 43(B) of the oscillation circuit is in a rectified rectangular wave form. This rectangular wave form can be directly inputted in a microcomputer provided in a controller of the washer to determined a frequency.

Figure 8:
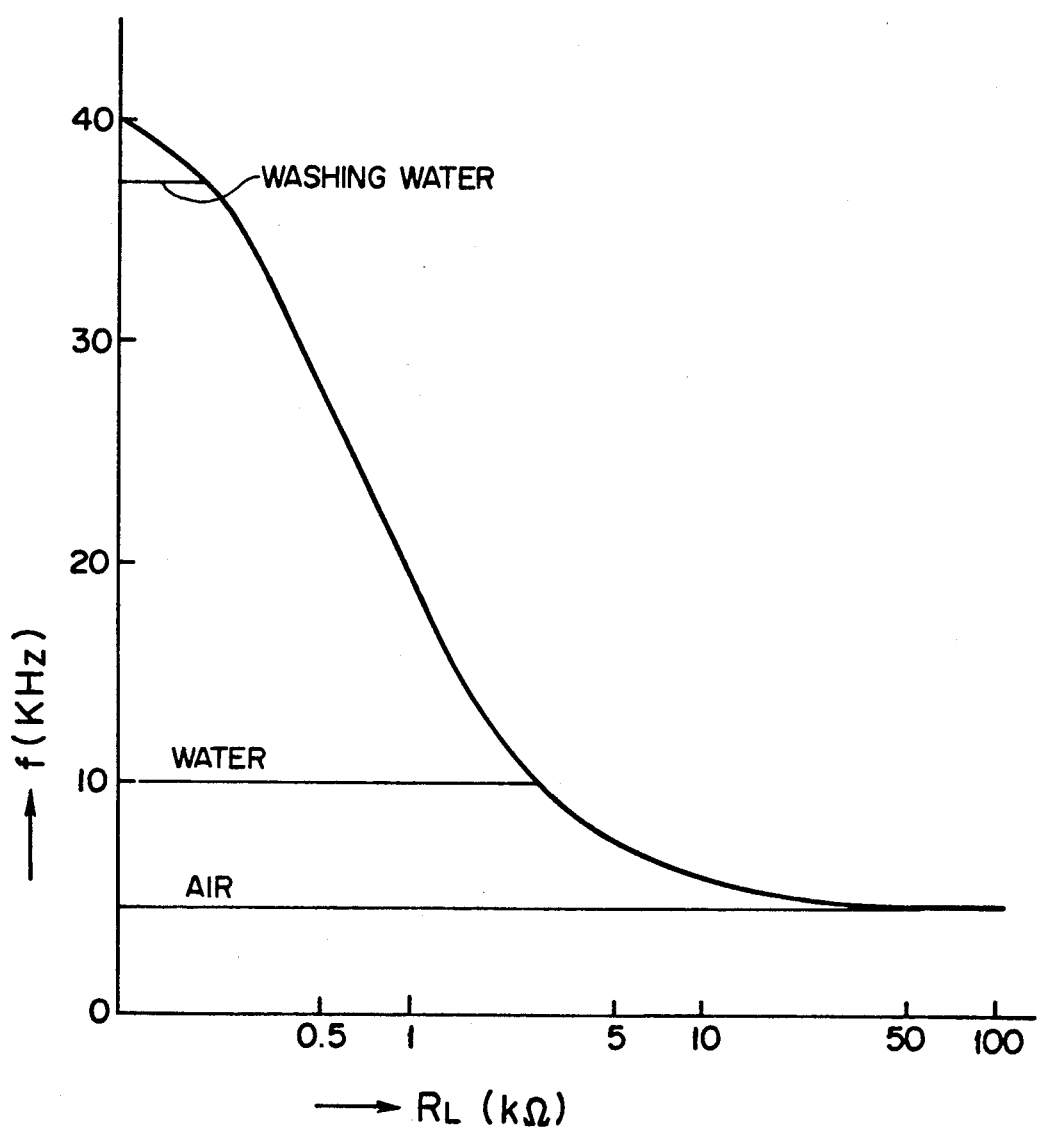
FIG. 8 is a graphical illustration of a relationship between electric resistances detected by the sensor and oscillation frequencies.

As shown in FIG. 8, a frequency of the washing water containing a detergent is 38 KHz, a frequency of tap water is 10 KHz, and a frequency of air is 4.5 KHz. According to the invention, a frequency of the rectangular wave is counted by the microcomputer to judge the soiled condition of the washing water.

A washing operation consists of a washing step, a rinsing step and a final dehydrating step. In the washing step, water is supplied in the water storage tank to a predetermined level, and the agitation blade 6 is rotated for washing. After the washing step is completed, the drain valve 13 is opened to discharge the water from the washing machine. Subsequently, the washing/dehydrating tank 5 is rotated at a high speed together with the agitation blade 6 for dehydrating. Then, the washing operation proceeds to the rinsing step. In the rinsing step, clean water is first supplied to a predetermined level, and the agitation blade 6 is rotated again for rinsing. After the rinsing step is completed, the drain valve 13 is opened again to discharge the water. Thereafter, the washing/dehydrating tank 5 is rotated at a high speed together with the agitation blade 6 for dehydrating. Usually, this rinsing step is repeated twice. The dehydration after the last rinsing step is the final operation step. When this final dehydrating step is completed, the washing operation is finished.

In the above-described washing operation, the electric conductivity detecting sensor 15 operates as follows.

First, in the washing step, when the agitation blade 6 starts to rotate, a detergent and certain soil of the washing are dissolved in the washing water. The electric conductivity of the washing water at this time and the conductivity of the washing water before rotation of the agitation blade 6 are respectively detected by the sensor 15 to be compared and calculated in the microcomputer of the controller. In the illustrated embodiment, since an operation time for washing is decided according to the above comparison and calculation, an appropriate washing operation, depending on a soiled condition of the washing, can be performed.

In the rinsing step, when the agitation blade 6 starts to rotate, the detergent contained in the washing is dissolved in the rinsing water. The electric conductivity of the rinsing water at this time and the conductivity of the rinsing water before rotation of the agitation blade 6 are respectively detected by the sensor 15 to be compared and calculated in the microcomputer of the controller. In this manner, the number of rinsing cycles is determined to carry out an appropriate rinsing operation in accordance with the detergent contained in the washing.

In the final dehydrating step, when the dehydrating operation progresses, the resistance representative of the electric conductivity between the electrodes of the sensor 15 increases while the oscillation frequency decreases. A period of time which is required for the oscillation frequency to become a predetermined value is measured. On the basis of the thus measured period of time, a necessary time for the dehydrating operation is decided and, therefore, an appropriate dehydrating operation can be performed.

The electric conductivity detection sensor 15 is located on the outer periphery of the bottom of the water storage tank 7. This is because the sensor 15 is required to detect the conductivity of the water even when the washing operation with the washing water of a low level or even during the dehydrating operation after drainage of the washing water and, therefore, it has to be situated on the bottom of the water storage tank 7. Further, the position in the outer periphery is more suitable for detection of a flow of the dehydrated water than the center of the bottom of the water storage tank. Accordingly, the detection accuracy is further improved. Additionally, maintenance of the sensor 15 can be facilitated when it is located at the outer peripheral position.

It has also been considered to provide the sensor 15 in a drain passage which leads to the drain valve 13. However, it has been found that the detection accuracy in this case is undesirably low. This is because the water stagnates in the drain passage water and moves at an outer peripheral area while moving in an outer peripheral area of the water storage tank 7. It takes a long period of time until the water in which the detergent and the soil are dissolved comes into the drain passage, so that the detection accuracy is low.

Because the sensor 15 is arranged such that the opposing surfaces of the pair of electrodes are substantially perpendicular to the rotating direction of the washing/dehydrating tank 5, the opposing surfaces of the electrodes 25 extend along a flow of water when the washing water is drained. Therefore, ravelings or the like do not twine around the electrodes to effect the detection accuracy.

The electric conductivity detection sensor 15 is constructed such that the electrode holder 19 is of a substantially cylindrically shaped contour and has the groove 23 extending inwardly from a top end thereof. The plate-like electrodes 25 are arranged on the respective, opposite inner walls of the groove 23 and the top end portion of the electrode holder 19 is spherically shaped. Accordingly, the ravelings hardly twine about the sensor not to affect the detection accuracy.

Moreover, the dehydrated water falling along the inner surface of the water storage tank 7 concentrates on the recessed portion 16 where the sensor 15 is attached. Accordingly, the detection accuracy is further improved.

The electrode holder 19 of the sensor 15 has the groove 23 formed at a top end thereof. The plate-like electrodes 25 are arranged on the respective, opposite inner walls of the groove 23, and the upright separation wall 24 is provided at the center of the bottom of the groove 23. Because the upright separation wall 24 prevents the soil and dregs of the detergent from sticking to the bottom of the groove 23, the detection accuracy can be favorably ensured.

The portion where the sensor 15 is attached is in the shape of the recessed portion 16 which is similar to an ellipse when viewed from the inner side of the water storage tank. The recessed portion 16 is arranged such that the longitudinal axis thereof is substantially perpendicular to the rotating direction of the washing/dehydrating tank 7. Accordingly, the water can flow smoothly through the recessed portion 16. Furthermore, the water passing groove 17 is formed at the lower end of the recessed portion 16 to makes the water to flow more smoothly.

Although the invention has been described in conjunction with the embodiment of a fully automatic washing machine of a vertical type, the present invention can be applied also to a drum washing machine of a horizontal type. Further, the electric conductivity detecting sensor of the invention can be used in other apparatuses other than a washing machine. For instance, the sensor is applicable to detection of a quality of water in a water conduit or a reservoir.

What is claimed is:

1. A washing machine comprising a water storage tank, a washing/dehydrating tank rotatably provided in the water storage tank, an agitation blade arranged in the washing/dehydrating tank, a motor for driving the washing/dehydrating tank and the agitation blade for rotation, and a sensor for detecting an electric conductivity of washing water to control an operation of the washing machine, wherein said sensor is provided with a pair of electrodes and is attached to said water storage tank in such a manner that opposite surfaces of said electrodes are exposed to the washing water within said water storage tank, and wherein said water storage tank is provided with a portion outwardly recessed, and said sensor is mounted in said recessed portion such that the opposing surfaces of said electrodes are faced inwardly of said recessed portion.

2. A washing machine according to claim 1, wherein said sensor is arranged so as not to extend beyond a top end of said recessed portion.

3. A washing machine according to claim 1, wherein said pair of electrodes are formed in plate-like shapes and arranged in a face to face manner with each other, and the opposing surfaces of said electrodes are substantially perpendicular to a direction of rotation of said washing/dehydrating tank.

4. A washing machine comprising a water storage tank, a washing/dehydrating tank rotatably provided in the water storage tank, an agitation blade arranged in the washing/dehydrating tank, a motor for driving the washing/dehydrating tank and the agitation blade for rotation, and a sensor for detecting an electric conductivity of washing water to control an operation of the washing machine, wherein said sensor is provided with a pair of electrodes attached to said water storage tank in such a manner that opposite surfaces of said electrodes are exposed to the washing water within said water storage tank, and wherein a portion outwardly recessed is provided in a corner of said water storage tank, which corner extends upright from the bottom of said water storage tank, said conductivity detecting sensor is received in said recess portion such that the opposing surfaces of said electrodes are faced inwardly of said recessed portion, said recessed portion is formed in a shape similar to an ellipse, as viewed from an inner side of said water storage tank, and said recessed portion is disposed such that a longitudinal axis of said recessed portion is substantially perpendicular to a direction of rotation of said washing/dehydrating tank.

5. A washing machine according to claim 4, wherein said recessed portion has a water passing groove formed at a lower end of said recessed portion.

6. A washing machine comprising a washing/dehydrating tank, a water storage tank receiving the washing/dehydrating therein and a sensor casing fashioned of a synthetic resin, said sensor casing being formed with a holder having a substantially cylindrical shaped contour, said sensor being adapted to detect an electric conductivity of washing water in the washing-/dehydrating tank and the water storage tank, wherein said sensor includes a pair of electrodes accommodated in said holder to monitor a change of electric resistance representative of the electrical conductivity of the washing water between the pair of electrodes thereby controlling an operation of the washing machine, said holder having a groove formed so as to extend inwardly from a top end of said holder, said pair of electrodes being fashioned as plate-like electrodes arranged on respective opposite inner walls of said groove, and wherein a top end of said holder is formed in a substantially spherical shape.

7. A washing machine according to claim 6, wherein each of said electrodes is coated with a layer of an elastic material, said electrodes being further coated on said coating layer with a synthetic layer similar to that of said sensor casing and being held inside said holder.

8. A washing machine according to claim 6, further comprising a circuit board having electronic component parts mounted thereon, a housing section integrally formed in said sensor casing for receiving said circuit board therein, and a layer of synthetic material for sealing said circuit board.

9. A washing machine according to claim 6, further comprising a CR oscillation circuit including an electric resistance of the conductivity of the washing water between the electrodes and provided in said sensor casing.

10. A washing machine according to claim 9, wherein said CR oscillation circuit includes inverters.

11. A washing machine according to claim 6, further comprising an insulation transformer including a primary coil and a secondary coil, said primary being connected to said electrodes, wherein a variation in electric resistance between said electrodes is outputted from such secondary.

12. A washing machine according to claim 11, wherein said primary coil has a number of turns less than a number of turns of the secondary coil.

13. A washing machine according to claim 6, wherein an upright separation portion extends along inner walls of said groove at a center of a bottom of said groove.

14. A washing machine comprising, a washing/dehydrating tank, a water storage tank, receiving the washing/dehydrating tank therein, an agitation blade rotatably mounted on an inner bottom portion of the washing/dehydrating tank, a motor for driving the washing/dehydrating tank and the agitation blade, and a sensor for detection of an electric conductivity of washing water in the washing/dehydrating tank and the water storage tank, wherein said sensor is provided with a pair of electrodes to monitor a change of an electric resistance representative of the electric conductivity of the washing water between the electrodes thereby controlling an operation of the washing machine, and wherein said sensor includes a sensor casing which is made of a synthetic resin, said sensor casing is formed with an electrode holder which has a contour of a substantially cylindrical shape, said electrode holder has a groove formed to extend inwardly from a top end of said holder, said sensor includes the plate-like electrodes arranged on respective opposite inner walls of said groove, and the top end of said electrode holder is formed in a substantially spherical shape.

* * * * *